(12) United States Patent
Ooshima

(10) Patent No.: US 8,842,804 B2
(45) Date of Patent: Sep. 23, 2014

(54) X-RAY COMPUTED TOMOGRAPHY APPARATUS

(75) Inventor: Noriyuki Ooshima, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 259 days.

(21) Appl. No.: 13/421,176

(22) Filed: Mar. 15, 2012

(65) Prior Publication Data

US 2012/0177172 A1 Jul. 12, 2012

Related U.S. Application Data

(63) Continuation of application No. PCT/JP2012/050338, filed on Jan. 11, 2012.

(30) Foreign Application Priority Data

Jan. 12, 2011 (JP) ................................. 2011-004149

(51) Int. Cl.
*A61B 6/03* (2006.01)
*A61B 6/02* (2006.01)
*A61B 6/00* (2006.01)

(52) U.S. Cl.
CPC ................ *A61B 6/032* (2013.01); *A61B 6/027* (2013.01); *A61B 6/547* (2013.01)
USPC ............................................. 378/15; 378/20

(58) Field of Classification Search
USPC ................. 378/4, 13, 14, 15, 16, 20
See application file for complete search history.

(56) References Cited

U.S. PATENT DOCUMENTS 4,789,929 A * 12/1988 Nishimura et al. ............. 378/15

FOREIGN PATENT DOCUMENTS

| JP | 53-114375 | 10/1978 |
|---|---|---|
| JP | 60-207645 | 10/1985 |
| JP | 6-78916 | 3/1994 |
| JP | 09-285461 | 11/1997 |
| JP | 9-285461 | 11/1997 |
| JP | 11-89828 | 4/1999 |
| JP | 2008-17964 | 1/2008 |
| JP | 2009-160270 | 7/2009 |

OTHER PUBLICATIONS

International Search Report issued Jul. 19, 2012 in PCT/JP2012/050338 filed Jan. 11, 2012.
Japanese International Search Report mailed Feb. 7, 2012, in PCT/JP2012/050338 filed Jan. 11, 2012.
Japanese Written Opinion mailed Feb. 7, 2012, in PCT/JP2012/050338 filed Jan. 11, 2012.

* cited by examiner

*Primary Examiner* — Hoon Song
(74) *Attorney, Agent, or Firm* — Oblon, Spivak, McClelland, Maier & Neustadt, L.L.P.

(57) ABSTRACT

According to one embodiment, a position determination unit determines a top position at a projection data acquisition start time P by a user instruction. A first angle determination unit determines a first rotational angle at the time P by a user instruction. A second angle determination unit determines a second rotational angle at a top movement start time Q and a time interval from the time Q to the time P. A control unit controls a first driving unit to rotate the X-ray tube, controls a second driving unit to make a top start moving in response to arrival of the X-ray tube at the second rotational angle, and controls a DAS to start acquiring projection data in response to arrival of the top at the top position.

6 Claims, 7 Drawing Sheets

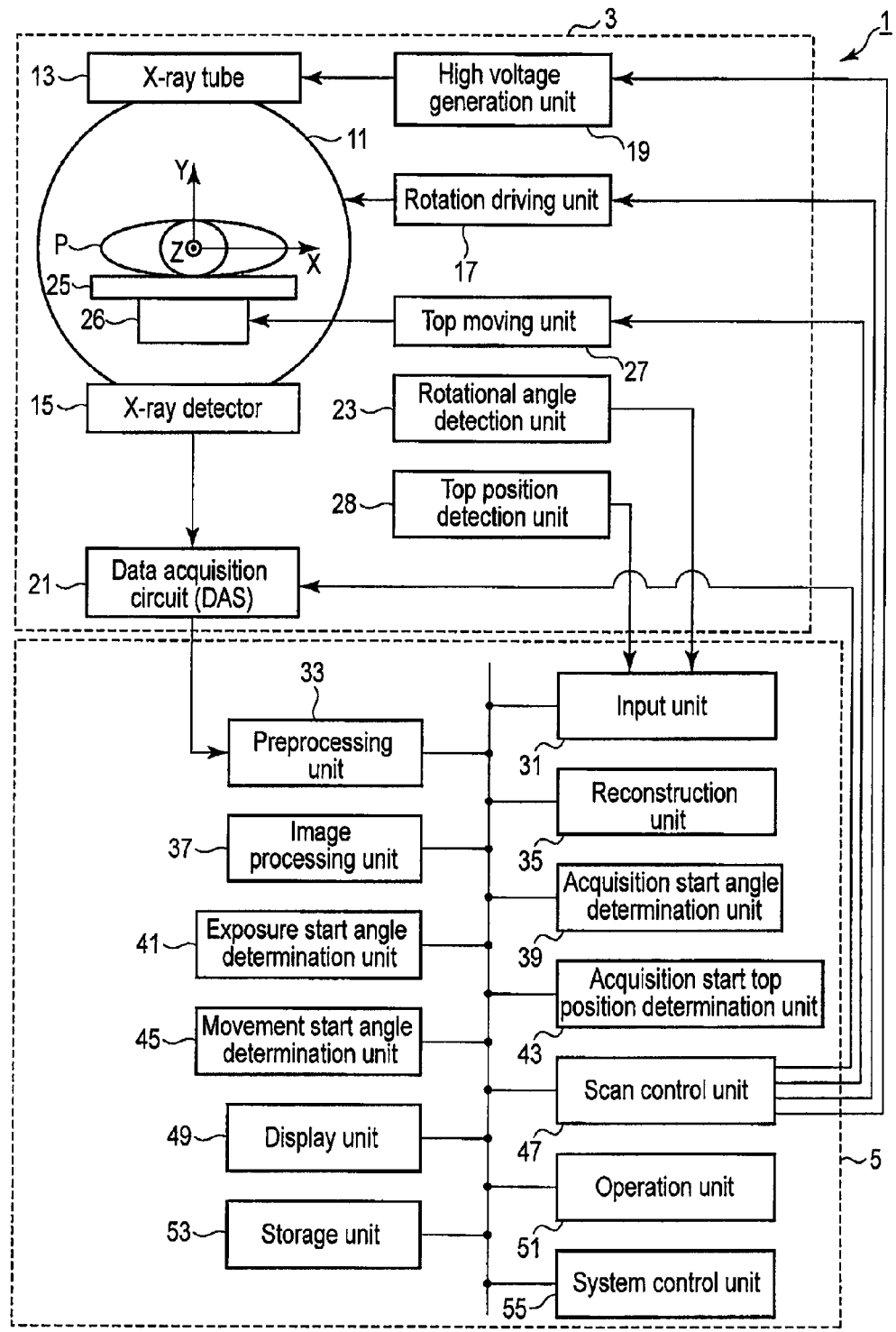
F I G. 1

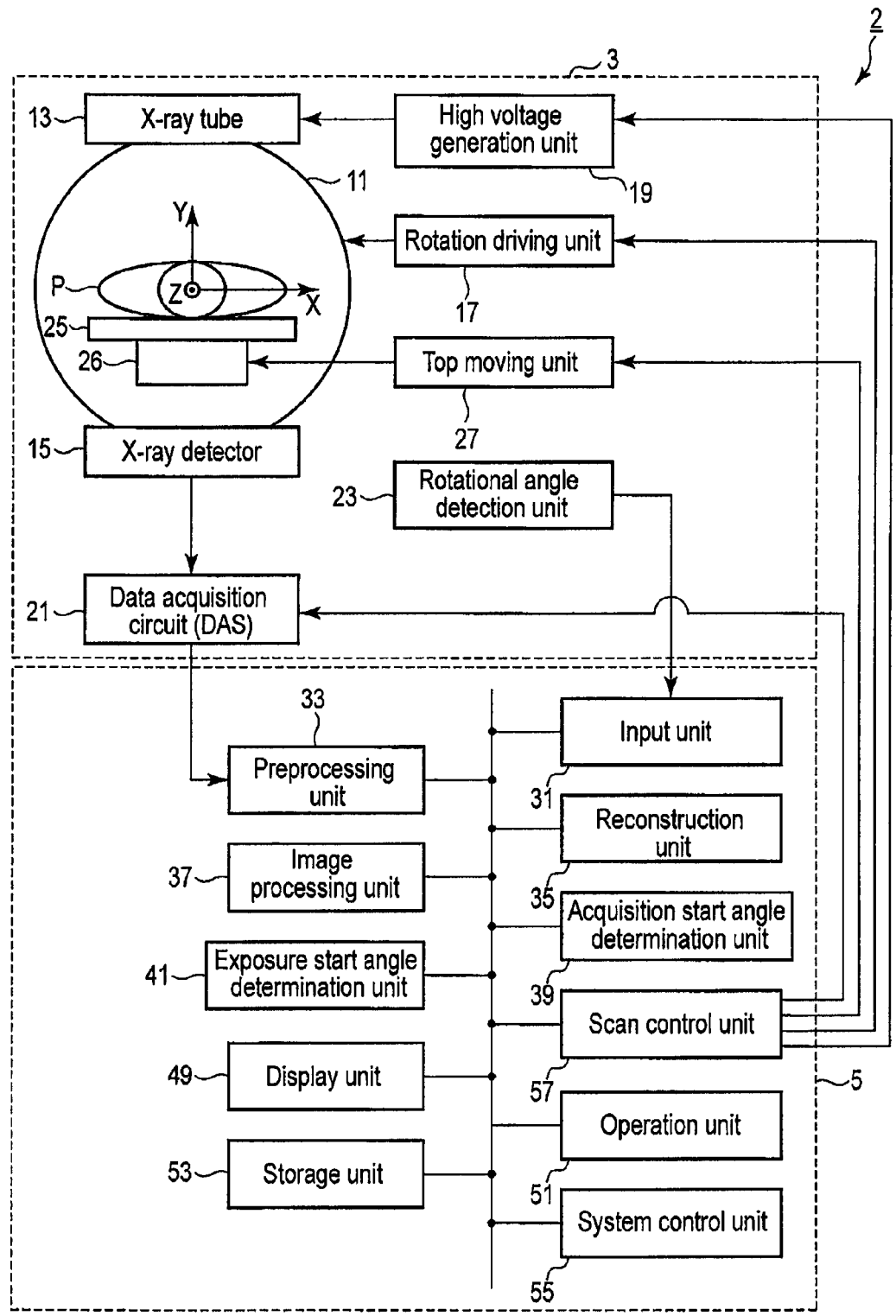
F I G. 5

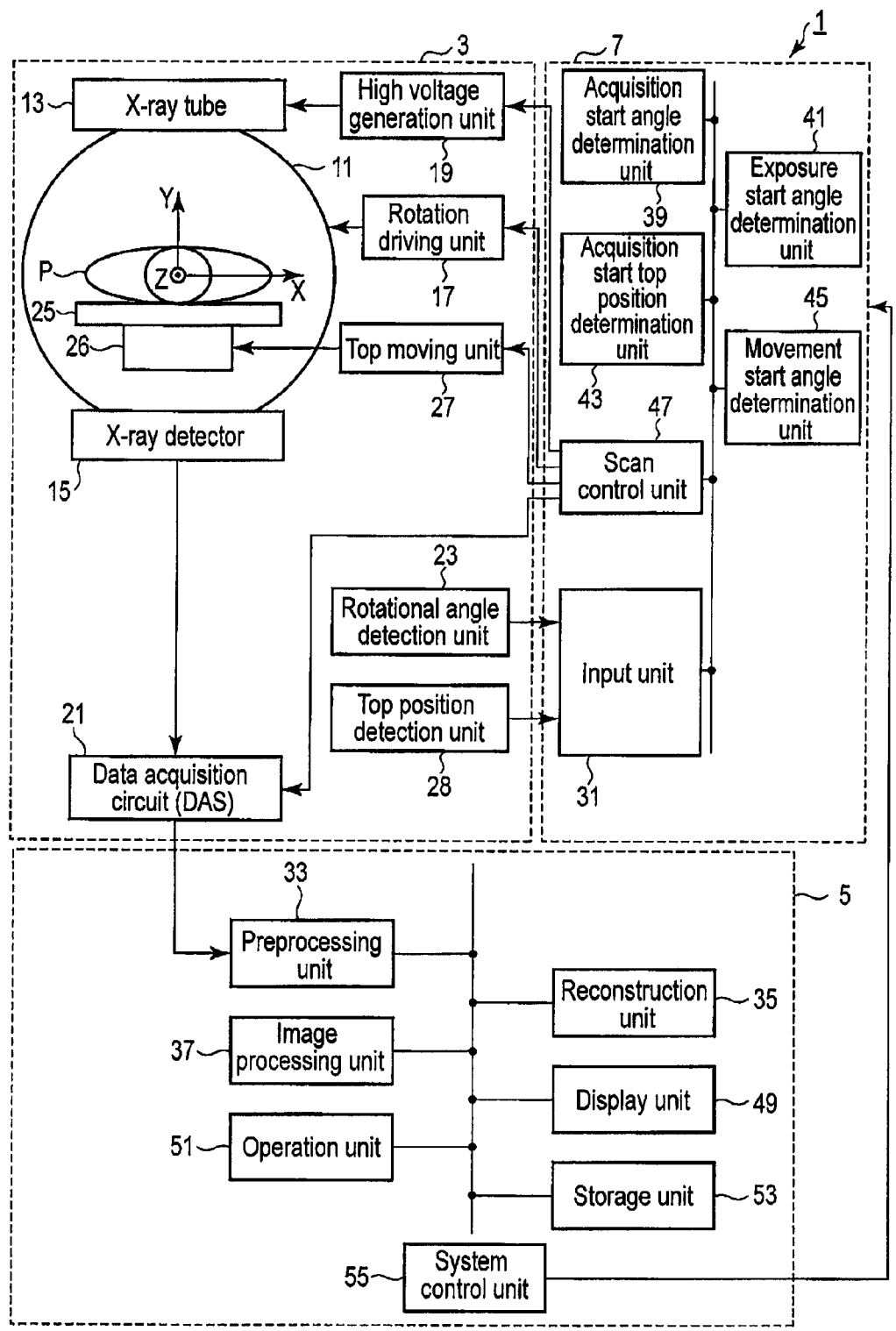
F I G. 8

X-RAY COMPUTED TOMOGRAPHY APPARATUS

CROSS REFERENCE TO RELATED APPLICATIONS

This application is a Continuation Application of PCT Application No. PCT/JP2012/050338, filed Jan. 11, 2012 and based upon and claiming the benefit of priority from prior Japanese Patent Application No. 2011-004149, filed Jan. 12, 2011, the entire contents of all of which are incorporated herein by reference.

FIELD

Embodiments described herein relate generally to an X-ray computed tomography apparatus.

BACKGROUND

An X-ray computed tomography apparatus executes controlled-orbit scanning of starting acquiring projection data by being triggered by the arrival of the X-ray tube at a specific rotational angle. This allows to start acquiring projection data from the same rotational angle if acquisition conditions such as a tube current and a top speed are the same. Under different acquisition conditions, however, the apparatus starts acquiring projection data from different rotational angles.

It is an object to provide an X-ray computed tomography apparatus which can start acquiring projection data from an arbitrary top position or rotational angle.

BRIEF DESCRIPTION OF THE DRAWINGS

FIG. 1 is a block diagram showing the arrangement of an X-ray computed tomography apparatus according to the first embodiment.

FIG. 5 is a block diagram showing the arrangement of an X-ray computed tomography apparatus according to the second embodiment.

FIG. 8 is a block diagram showing the arrangement of an X-ray computed tomography apparatus according to a modification of this embodiment.

DETAILED DESCRIPTION

Figure 2:
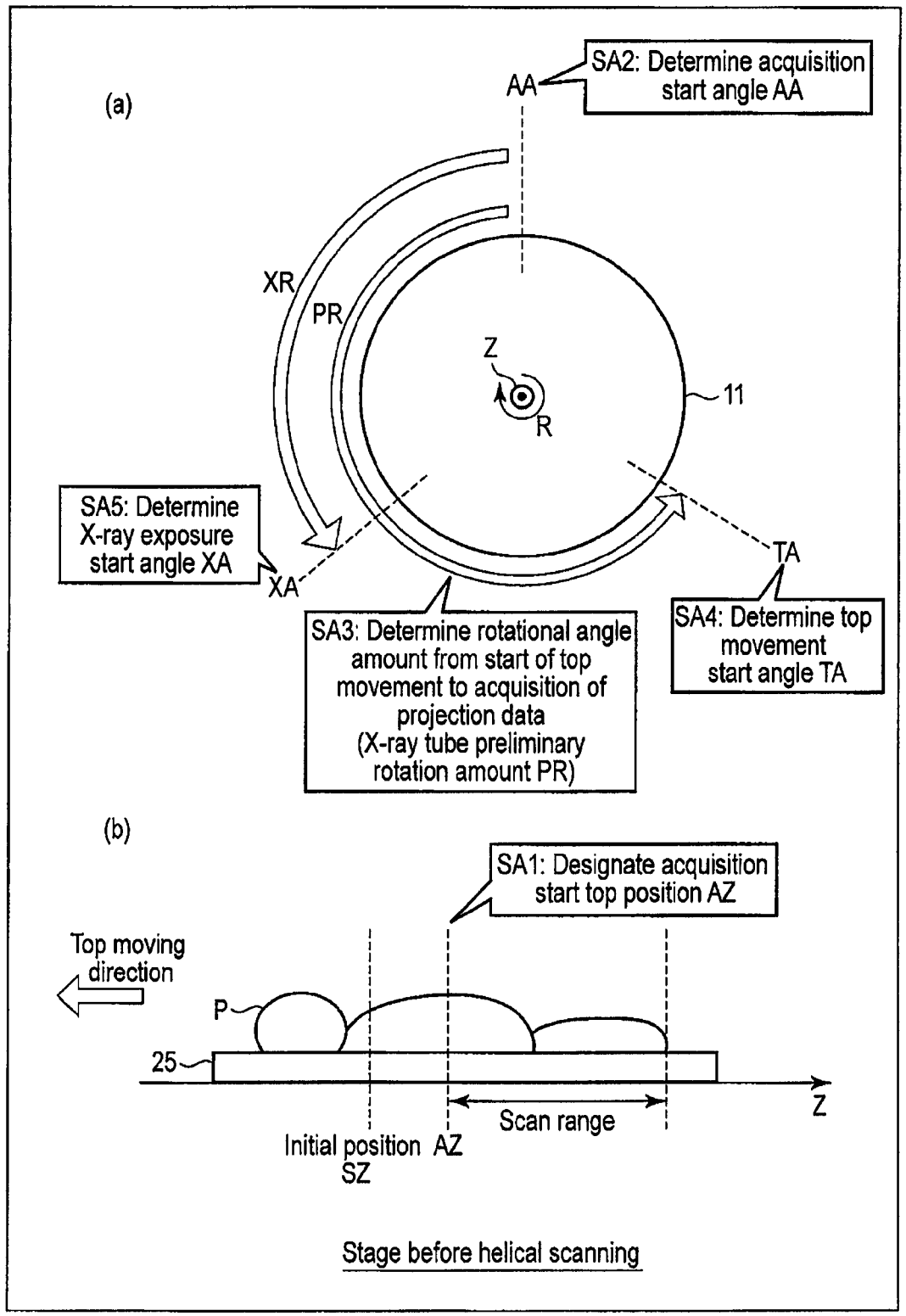
FIG. 2 is a view for explaining an example of operation at the stage before helical scanning by the X-ray computed tomography apparatus in FIG. 1.

In general, according to one embodiment, an X-ray computed tomography apparatus includes an X-ray tube, a detector, a first support mechanism, a first driving unit, a top, a second support mechanism, a second driving unit, an acquisition unit, a position determination unit, a first angle determination unit, a second angle determination unit, and a control unit. The X-ray tube generates X-rays. The detector detects X-rays which are generated from the X-ray tube and transmitted through a subject. The first support mechanism rotatably supports the X-ray tube and the detector. The first driving unit drives the first support mechanism to rotate the X-ray tube and the detector around the subject. The top makes the subject be placed thereon. The second support mechanism movably supports the top. The second driving unit drives the second support mechanism to move the top. The acquisition unit acquires projection data associated with the subject via the detector. The position determination unit determines a position of the top at an estimated start time of projection data acquisition by the acquisition unit in accordance with an instruction from a user. The first angle determination unit determines a first rotational angle of the X-ray tube at the estimated start time of projection data acquisition in accordance with an instruction from the user. The second angle determination unit determines a second rotational angle of the X-ray tube at an estimated start time of movement of the top based on the determined first rotational angle and a time interval from the estimated start time of movement to the estimated start time of projection data acquisition. The control unit controls the first driving unit to rotate the X-ray tube around the subject, controls the second driving unit to make the top start moving in response to arrival of the X-ray tube at the determined second rotational angle, and controls the acquisition unit to start acquiring projection data in response to arrival of the top at the determined position of the top.

X-ray computed tomography apparatuses according to the embodiments will be described below with reference to the accompanying drawings.

The scanning schemes used by the X-ray computed tomography apparatus include conventional scanning and helical scanning. In conventional scanning, the X-ray tube traces a circular orbit around a subject without being accompanied by the movement of the top. In helical scanning, the X-ray tube traces a helical orbit around a subject accompanied by the movement of the top. The X-ray computed tomography apparatus partly differs in arrangement depending on whether to perform conventional scanning or helical scanning. The first embodiment will exemplify an X-ray computed tomography apparatus which executes helical scanning. The second embodiment will exemplify an X-ray computed tomography apparatus which executes conventional scanning.

First Embodiment

FIG. 1 is a block diagram showing the arrangement of an X-ray computed tomography apparatus 1 according to the first embodiment. As shown in FIG. 1, the X-ray computed tomography apparatus 1 includes a gantry 3 and a console 5.

An annular or disk-like rotating frame 11 is mounted on the gantry 3. The rotating frame 11 supports an X-ray tube 13 and an X-ray detector 15 to allow them to rotate about a subject P to be examined. A slip ring mechanism (not shown) is used for signal and power transmission. More specifically, the rotating frame 11 is electrically connected to the fixed portion of the gantry 3 via the brush (not shown) of the slip ring mechanism. The X-ray detector 15 faces the X-ray tube 13 through an imaging area. The fixing portion is electrically connected to a rotation driving unit 17. The rotation driving unit 17 rotates the rotating frame 11 about a rotation axis Z and rotates the X-ray tube 13 and the X-ray detector 15 about the subject P under the control of a scan control unit 47 in the console 5.

Note that the Z-axis is defined as the rotation axis of the rotating frame 11. The Y-axis is defined as an axis connecting the X-ray focus of the X-ray tube 13 and the center of the X-ray detection surface of the X-ray detector 15. The Y-axis is perpendicular to the Z-axis. The X-axis is defined as an axis perpendicular to the Y-axis and the Z-axis. As described above, an xyz orthogonal coordinate system forms a rotating coordinate system which rotates together with the rotation of the X-ray tube 13.

The X-ray tube 13 is electrically connected to a high voltage generation unit 19. The X-ray tube 13 generates X-rays upon receiving a high voltage applied from the high voltage generation unit 19. The high voltage generation unit 19 applies a high voltage to the X-ray tube 13 under the control of the scan control unit 47.

The X-ray detector 15 detects X-rays which are generated from the X-ray tube 13 and transmitted through the subject P. The X-ray detector 15 then generates an analog current signal corresponding to the dose of detected X-rays. The X-ray detector 15 is connected to a data acquisition circuit 21 (DAS). The data acquisition circuit 21 acquires projection data associated with the subject via the X-ray detector 15. More specifically, the data acquisition circuit 21 reads out a current signal from the X-ray detector 15 and generates digital projection data by processing the readout current signal under the control of a scan control unit 47. The generated projection data is supplied to a preprocessing unit 33 of the console 5 via a slip ring mechanism (not shown).

The gantry 3 includes a rotational angle detection unit 23. The rotational angle detection unit 23 is implemented by a magnetic sensor, optical sensor, or position detection encoder (rotary encoder). The rotational angle detection unit 23 detects that the rotational angle of the rotating frame 11 about the Z-axis coincides with a specific angle and outputs an electrical signal (rotational angle signal) indicating the corresponding information. As the specific angle, an exposure start angle or acquisition start angle to be described later is suitably set. For example, the rotational angle detection unit 23 may be fixed to part of the rotating frame 11 which corresponds to this specific angle. The output rotational angle signal is supplied into the console 5 via an input unit 31.

In this case, when the X-ray tube 13 is located at the highest position on the rotating frame 11, the rotational angle of the X-ray tube 13 is defined to be 0°, whereas when the X-ray tube 13 is located at the lowest position on the rotating frame 11, the rotational angle of the X-ray tube 13 is defined to be 180°.

The subject P is placed on a top 25. The top 25 is supported by a top support mechanism 26 so as to be movable along the Z-axis. Typically, the top support mechanism 26 supports the top 25 so as to make the long axis of the top 25 parallel to the Z-axis. The top 25 and the top support mechanism 26 constitute a bed. The top support mechanism 26 is electrically connected to a top moving unit 27. The top moving unit 27 drives the top support mechanism 26 and moves the top 25 along the Z-axis under the control of the scan control unit 47.

A top position detection unit 28 is attached to the top 25 or the top support mechanism 26. The top position detection unit 28 is implemented by a magnetic sensor, optical sensor, or position detection encoder (rotary encoder). The top position detection unit 28 detects that the top position coincides with a specific position, and outputs an electrical signal (top position signal) indicating the corresponding information. The output top position signal is supplied into the console 5 via the input unit 31. As this specific position, an acquisition start top position (to be described later) is suitably set. The top position detection unit 28 is fixed to, for example, part of the top 25 or top moving unit 27 which corresponds to the specific position.

Assume that a top position is defined by the position of a reference point on the top 25 in the Z-axis direction. The position of this reference point is defined as a point on the top 25 which intersects a line connecting the X-ray focus of the X-ray tube 13 and the center of the surface of the X-ray detector 15.

As shown in FIG. 1, the console 5 includes the input unit 31, the preprocessing unit 33, a reconstruction unit 35, an image processing unit 37, an acquisition start angle determination unit 39, an exposure start angle determination unit 41, the acquisition start top position determination unit 43, the movement start angle determination unit 45, the scan control unit 47, a display unit 49, an operation unit 51, a storage unit 53, and a system control unit 55.

The input unit 31 is an interface used for communication between the gantry 3 and the console 5. More specifically, the input unit 31 receives a rotational angle from the rotational angle detection unit 23. The input unit 31 also receives a top position signal from the top position detection unit 28.

The preprocessing unit 33 performs logarithmic transformation and sensitivity correction for the projection data supplied from the data acquisition circuit 21. The reconstruction unit 35 reconstructs image data associated with the subject based on the preprocessed projection data. The image processing unit 37 performs various kinds of image processing for the image data.

The acquisition start angle determination unit 39 sets the rotational angle of the X-ray tube 13 at the estimated time of the start of acquisition of projection data by the data acquisition circuit 21 in accordance with the instruction issued by the user via the operation unit 51. The rotational angle of the X-ray tube 13 at the estimated time of the start of acquisition will be referred to as an acquisition start angle hereinafter.

The exposure start angle determination unit 41 determines the rotational angle of the X-ray tube at the estimated time of the start of generation of X-rays by the X-ray tube 13 based on an acquisition start angle and an X-ray stability time. The rotational angle of the X-ray tube 13 at the estimated time of the start of generation of X-rays will be referred to as an exposure start angle hereinafter.

An acquisition start top position determination unit 43 determines a top position at the estimated time of the start of acquisition of projection data by the data acquisition circuit 21 in accordance with the instruction issued by the user via the operation unit 51. The top position at the estimated time of the start of acquisition will be referred to as an acquisition start top position hereinafter.

A movement start angle determination unit 45 determines the rotational angle of the X-ray tube 13 at the estimated time of the start of movement of the top 25 based on the acquisition start angle and top preliminary movement time decided by the acquisition start top position determination unit 43. The rotational angle of the X-ray tube 13 at the estimated time of the start of movement will be referred to as a top movement start angle hereinafter. The top preliminary movement time is defined to be the time interval from the estimated time of the start of movement of the top 25 to the estimated time of the start of acquisition of projection data.

The scan control unit 47 controls the data acquisition circuit 21, the rotation driving unit 17, the high voltage generation unit 19, and the top moving unit 27 to execute helical scanning from the acquisition start top position (or the acquisition start angle). More specifically, first of all, the scan control unit 47 rotates the rotating frame 11 by controlling the rotation driving unit 17 in response to the rotation start instruction issued by the user via the operation unit 51. The scan control unit 47 then starts moving the top 25 by controlling the top moving unit 27 in response to the arrival of the X-ray tube 13 at the top movement start angle. The scan control unit 47 generates X-rays by controlling the high voltage generation unit 19 in response to the arrival of the X-ray tube 13 at the exposure start angle. The scan control unit 47 starts acquiring projection data by controlling the data acquisition circuit 21 in response to the arrival of the top 25 at the acquisition start top position.

The display unit 49 displays an image corresponding to the image data reconstructed by the reconstruction unit 35 and an image corresponding to the image data processed by the image processing unit 37 on the display. The operation unit 51 accepts various kinds of commands and information inputs from the operator with input devices. The storage unit 53 stores image data. The storage unit 53 stores control programs for the X-ray computed tomography apparatus 1. The system control unit 55 reads out control programs stored in the storage unit 53, expands the programs in the memory, and controls the respective units in accordance with the expanded control programs.

An example of the operation of the X-ray computed tomography apparatus 1 will be described next.

An example of the operation of the X-ray computed tomography apparatus 1 at the stage before helical scanning will be described first with reference to FIG. 2. The stage before helical scanning is provided to determine an acquisition start top position, exposure start angle, acquisition start angle, top movement start angle, and the like. Assume that at the stage before helical scanning, the scan control unit 47 has set acquisition conditions such as the rotational speed of the rotating frame 11, X-ray conditions, and the moving speed of the top 25. The set value of the rotational speed of the rotating frame 11 will be referred to as a set gantry speed. In addition, the set value of the speed of the top 25 when it moves at a constant speed will be referred to as a set top speed. X-ray conditions include all factors that influence the dose of X-rays, e.g., a tube current, a tube voltage, and the type of filament.

At the stage before helical scanning, first of all, the user designates a top position via the operation unit 51 or the like. The acquisition start top position determination unit 43 determines the top position designated by the user via the operation unit 51 as an acquisition start top position AZ (step SA1). The data of the determined top position AZ is supplied to the scan control unit 47. Typically, the top position AZ is determined in association with the setting of a scan range by a scan expert system. Note that the method of setting the top position AZ is not limited to this method. For example, the user may directly designate the coordinates or the like of a top position as the top position AZ via the operation unit 51.

In addition, at the stage before helical scanning, the user designates the rotational angle of projection data via the operation unit 51 or the like. The acquisition start angle determination unit 39 determines the designated rotational angle as an acquisition start angle AA (step SA2). It is possible to designate the acquisition start angle AA to an arbitrary rotational angle between 0° and 360°. The data of the acquisition start angle AA is supplied to the scan control unit 47.

Note that the method of designating an acquisition start angle is not limited to only the above method of directly designating a rotational angle. For example, the user may designate the body posture of the subject P. When the user designates the body posture of the subject P, the acquisition start angle determination unit 39 determines an acquisition start angle in accordance with the body posture of the subject P. For example, the unit 39 may determine an acquisition start angle in accordance with the body posture designated by the user using a table which associates the body postures of the subject P and acquisition start angles. More specifically, when the subject P lies on his/her left arm on the top 25, the acquisition start angle may be set to 30°. Likewise, when the subject P lies on his/her back, the acquisition start angle may be set to 120°. When the subject P lies on his/her right arm, the acquisition start angle may be set to 210°. When the subject P lies on his/her abdomen, the acquisition start angle may be set to 300°.

Note that the order of steps SA1 and SA2 is not limited to the above order. That is, step SA1 may be performed after step SA2.

When the apparatus performs steps SA1 and SA2, the movement start angle determination unit 45 determines a top movement start angle TA based on an acquisition start top position and a top preliminary movement time (steps SA3 and SA4).

Figure 3:
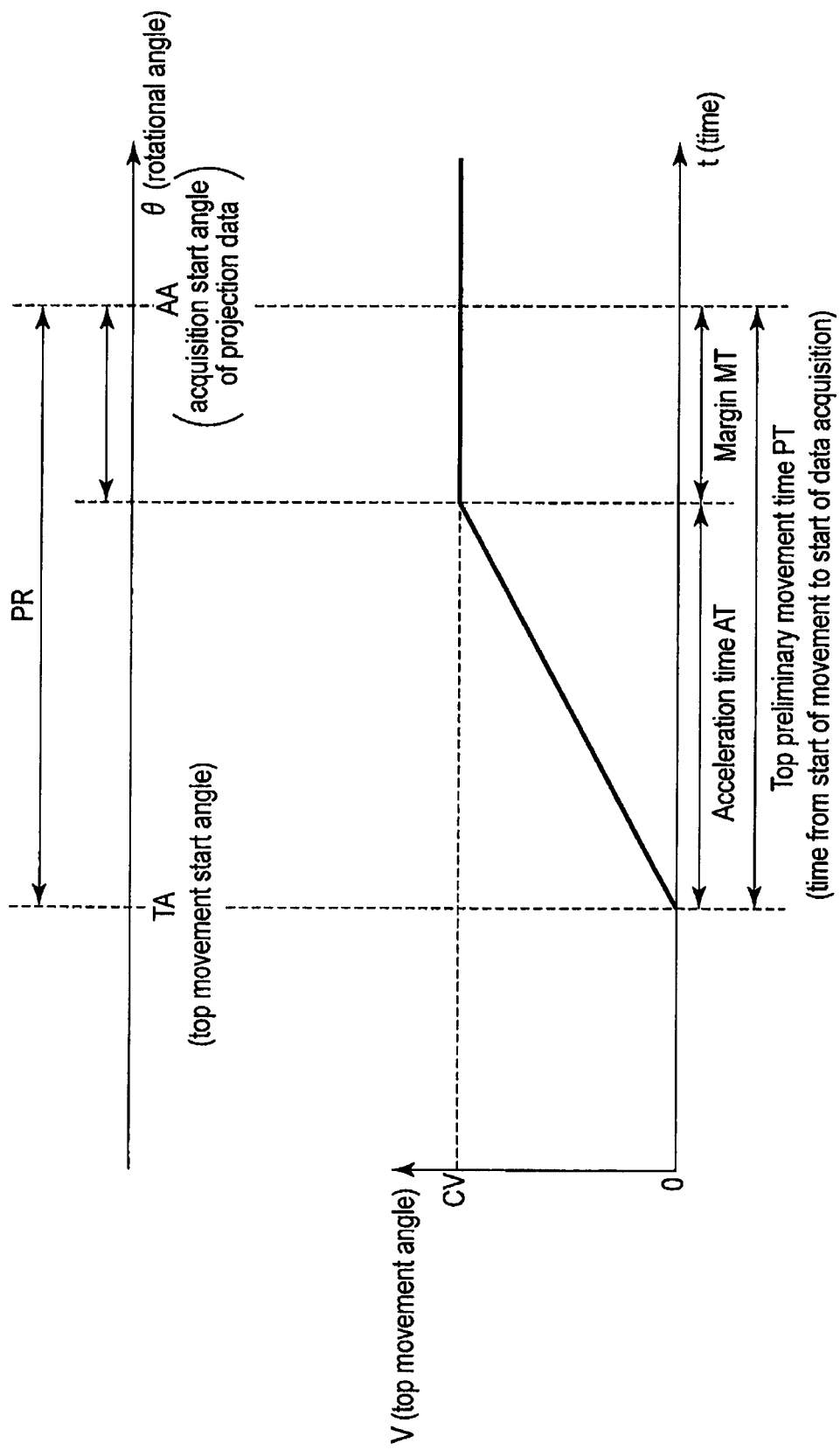
FIG. 3 is a graph for explaining determination processing for a movement start angle by a movement start angle determination unit in FIG. 1.

Determination processing for the top movement start angle TA by the movement start angle determination unit 45 will be described with reference to FIG. 3. As shown in FIG. 3, the top 25 moves from an initial position SZ to the acquisition start top position AZ at a top preliminary movement time PT. The top preliminary movement time PT includes an acceleration time AT and a margin MT. The acceleration time AT is defined to the time interval from the movement start time of the top 25 to a time point at which the top 25 reaches a set top speed CV. The top speed CV is the speed of the top during acquisition of projection data. The margin MT is defined as the time interval from a time point at which the moving speed of the top 25 reaches the set top speed CV to the projection data acquisition start time. In other words, the top preliminary movement time PT is equal to the time interval from the estimated time of the start of movement of the top to the estimated time of the start of acquisition of projection data.

At the stage of setting acquisition conditions, the scan control unit 47 has already set a top preliminary movement amount (the movement amount of the top 25 at the top preliminary movement time PT) and the set top speed CV. The movement start angle determination unit 45 calculates the top preliminary movement time PT based on the top preliminary movement amount and the set top speed CV. More specifically, the acceleration time AT and an acceleration movement amount (the movement amount of the top 25 at the acceleration time AT) AD are automatically determined in accordance with the set top speed CV. The top preliminary movement time PT is calculated by applying equation (1) to the acceleration time AT, a top preliminary movement amount PD, the acceleration movement amount AD, and the set top speed CV.

$$PT = AT + (PD - AD)/CV \tag{1}$$

Note that (PD−AD)/CV is equal to the margin MT.

Upon calculating the top preliminary movement time PT, the determination unit 45 determines an X-ray tube preliminary rotation amount PR based on the top speed CV and the set top preliminary movement time PT (step SA3). The X-ray tube preliminary rotation amount PR is defined as the rotational angle amount of the X-ray tube 13 from the top movement start time to the projection data acquisition start time. For example, the determination unit 45 determines the X-ray tube preliminary rotation amount PR by converting the set top preliminary movement time PT into a rotational angle in accordance with the top speed CV.

Upon determining the X-ray tube preliminary rotation amount PR, the determination unit 45 determines the top movement start angle TA based on the acquisition start angle AA and the X-ray tube preliminary rotation amount PR (step SA4). For example, the determination unit 45 calculates the top movement start angle TA by subtracting the X-ray tube preliminary rotation amount PR from the acquisition start angle AA. The data of the top preliminary movement time PT, the data of the top movement start angle TA, and the data of the X-ray tube preliminary rotation amount PR are supplied to the scan control unit 47.

As shown in FIG. 2, when the apparatus performs steps SA3 and SA4, the exposure start angle determination unit 41 determines an X-ray exposure start angle XA based on the acquisition start angle AA and the X-ray stability time (step SA5).

Determination processing for the X-ray exposure start angle XA by the exposure start angle determination unit 41 will be described in detail below. First of all, the determination unit 41 determines a rotational angle amount XR of the X-ray tube 13 within an X-ray stability time based on the acquisition start angle AA and the X-ray stability time. The X-ray stability time is the time required to stabilize the dose of X-rays from the time when the X-ray tube 13 starts generating X-rays. The determination unit 41 determines an X-ray stability time in accordance with X-ray conditions such as a tube current, tube voltage, and the type of filament. Alternatively, the determination unit 41 may determine an X-ray stability time by using a table which associates X-ray conditions with X-ray stability times. In addition, the determination unit 41 may determine an X-ray stability based on a set gantry speed and X-ray conditions. Upon determining an X-ray stability time, the determination unit 41 converts the X-ray stability time into the X-ray tube preliminary rotation amount PR by using the set gantry speed. For example, the determination unit 41 calculates the rotational angle amount XR by multiplying the set gantry speed by the X-ray stability time. Upon calculating the rotational angle amount XR, the determination unit 41 calculates the X-ray exposure start angle XA by subtracting the rotational angle amount XR from the acquisition start angle AA. Typically, the X-ray exposure start angle XA is less different from the acquisition start angle AA than the top movement start angle TA. This is because the X-ray stability time is shorter than the top preliminary movement time. The data of the X-ray exposure start angle XA is supplied to the scan control unit 47.

Note that the order of steps SA4 and SA5 is not limited to the above order. That is, the determination unit 41 may perform steps SA3, SA4, and SA5 in the order named, or may perform steps SA3, SA5, and SA4 in the order named.

Upon determining the acquisition start top position AZ, the acquisition start angle AA, the top movement start angle TA, and the X-ray exposure start angle XA in this manner, the apparatus finishes the stage before helical scanning.

Figure 4:
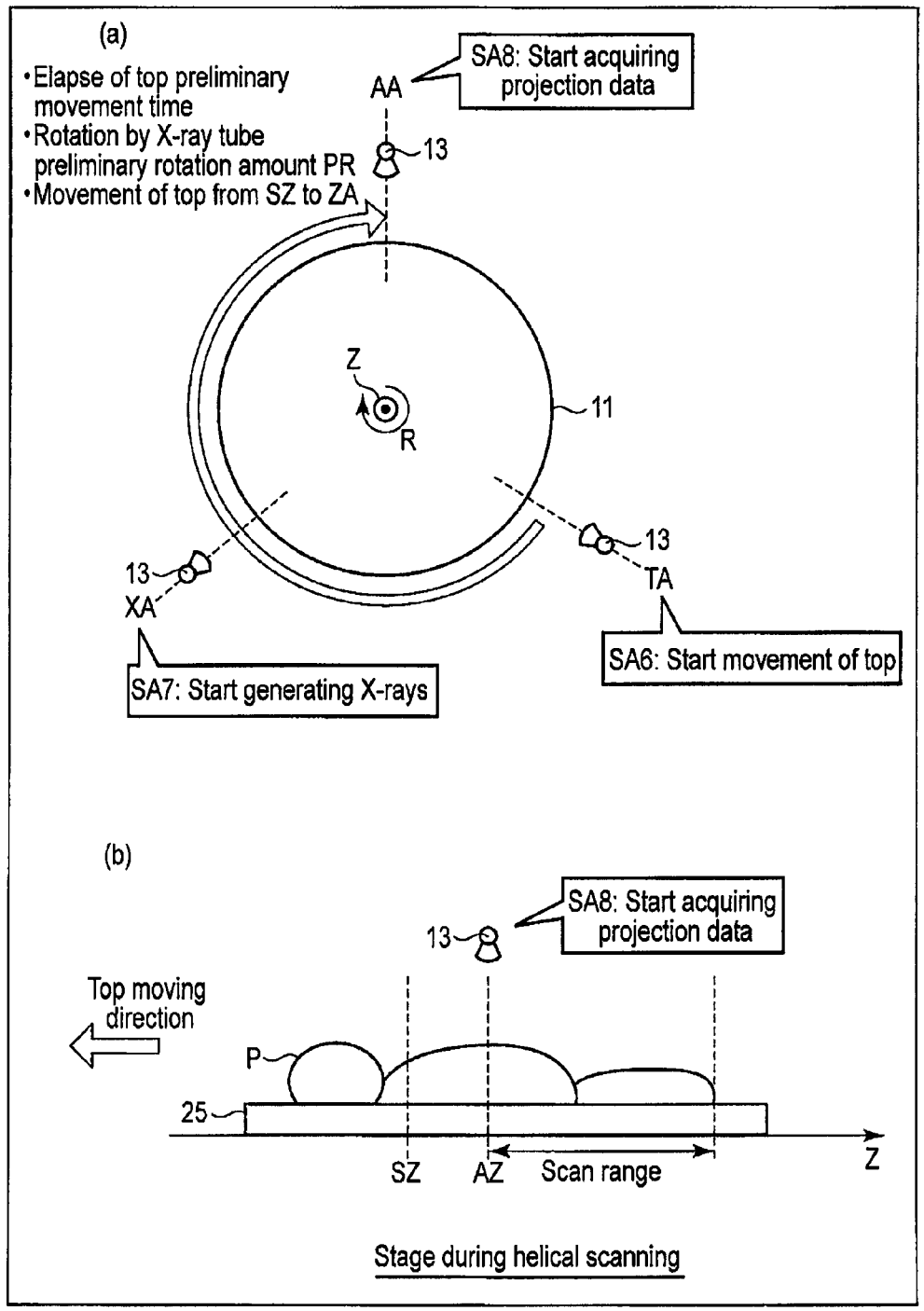
FIG. 4 is a view for explaining an example of operation at the stage during helical scanning by the X-ray computed tomography apparatus in FIG. 1.

An example of the operation of the X-ray computed tomography apparatus 1 at the stage during helical scanning will be described next with reference to FIG. 4. First of all, the scan control unit 47 controls the rotation driving unit 17 to rotate the rotating frame 11 in response to a timing when the user issues an instruction to start rotating the rotating frame 11 via the operation unit 51. The rotating frame 11 accelerates from the rotation start time to the set gantry speed, and then repeatedly and constantly rotates at the set gantry speed. When the rotational speed reaches the set gantry speed, the X-ray exposure start button of the operation unit 51 shifts to the pressable state. When the user presses the X-ray exposure start button, the scan control unit 47 waits until the X-ray tube 13 reaches the top movement start angle TA.

The scan control unit 47 controls the top moving unit 27 to start moving the top 25 in response to the arrival of the X-ray tube 13 at the top movement start angle TA (step SA6). The top 25 is placed at the initial position SZ at the movement start time, and starts moving from the initial position SZ to the acquisition start top position AZ relative to the above reference point.

When the top 25 starts moving, the scan control unit 47 waits until the X-ray tube 13 reaches the X-ray exposure start angle XA. The scan control unit 47 controls the high voltage generation unit 19 to make the X-ray tube 13 start generating X-rays in response to the arrival of the X-ray tube 13 at the X-ray exposure start angle XA (step SA7). The dose of X-rays is not stable immediately after the start of exposure because X-ray conditions such as a tube current value and filament temperature do not reach set values. Since the X-ray conditions are not changed at the stage during helical scanning and the stage before it, the dose of X-rays theoretically reaches a set value and stabilizes after the X-ray stability time from the exposure start time. In other words, when the X-ray tube 13 rotates from the X-ray exposure start angle XA by the X-ray stability rotational angle amount XR, the dose of X-rays stabilizes at the set value.

When the top 25 starts moving, the scan control unit 47 waits until the arrival of the top 25 at the acquisition start top position AZ. When the top 25 reaches the acquisition start top position AZ, the scan control unit 47 causes the data acquisition circuit 21 to start acquiring projection data (step SA8). Since the acquisition conditions are not changed at the stage during helical scanning and at the stage before it, the arrival of the top 25 at the acquisition start top position AZ can be regarded as the arrival of the X-ray tube 13 at the acquisition start angle AA. There are two methods of recognizing that the top 25 reaches the acquisition start top position AZ, that is, methods respectively based on 1. the top position and 2. the elapsed time from the top movement start time. The two recognition methods will be concretely described below.

Recognition method 1-1: When the top 25 starts moving, the scan control unit 47 measures the elapsed time from the movement start time point (the time point when the X-ray tube 13 has reached the top movement start angle TA), and waits for the elapse of the top preliminary movement time from the movement start time. In response to the elapse of the top preliminary movement time from the movement start time, the scan control unit 47 causes the data acquisition circuit 21 to start acquiring projection data. The acquisition conditions such as a set top speed and top preliminary movement amount are not changed at the stage during helical scanning and at the stage before it. Therefore, when the top preliminary movement time has elapsed from the movement start time, the top 25 can be regarded to be located at the acquisition start top position. That is, the scan control unit 47 regards the elapse of the top preliminary movement time from the movement start time as synonymous with the arrival of the top 25 at the acquisition start top position. Recognizing the arrival of the top 25 at the acquisition start top position from the elapsed time from the movement start time in this manner eliminates the necessity to use the top position detection unit 28 as in a recognition method 1-2. Therefore, the recognition method 1-1 allows to recognize the arrival of the top 25 at the acquisition start top position with a simple arrangement as compared with the recognition method 1-2.

Recognition Method 1-2: In addition to the top position detection unit 28 for detecting the movement start position of the top 25, the top position detection unit 28 for detecting the acquisition start top position is provided on the top 25 or the top support mechanism 26. Every time the top position reaches the acquisition start top position, the top position detection unit 28 supplies a top position signal indicating the corresponding information (to be referred to as an acquisition start signal hereinafter) to the scan control unit 47. When the top 25 reaches the movement start position, the scan control unit 47 waits until an acquisition start signal is supplied from the top position detection unit 28. In response to the reception of an acquisition start signal, the scan control unit 47 causes the data acquisition circuit 21 to start acquiring projection data via the X-ray detector 15. That is, the scan control unit 47 regards the arrival of an acquisition start signal as synonymous with the arrival of the top 25 at the acquisition start angle. Directly recognizing the arrival of the top 25 at the acquisition start top position based on the top position in this manner allows to start acquiring projection data from the acquisition start top position more reliably than the recognition method 1-1.

When the acquisition of projection data starts, the scan control unit 47 moves the top 25 from the acquisition start top position AZ by a scan range. When the top 25 moves by the scan range, the scan control unit 47 finishes helical scanning. That is, the scan control unit 47 controls the rotation driving unit 17 to stop the rotation of the rotating frame 11, controls the high voltage generation unit 19 to stop the generation of X-rays, controls the data acquisition circuit 21 to stop the acquisition of projection data, and controls the control processor 29 to stop the movement of the top 25.

The X-ray computed tomography apparatus 1 according to the first embodiment determines an arbitrary top position as an acquisition start top position in accordance with an instruction from the user in helical scanning. The X-ray computed tomography apparatus 1 determines a top movement start angle by using the determined acquisition start top position. At the time of helical scanning, the X-ray computed tomography apparatus 1 starts moving the top 25 in response to the arrival of the X-ray tube 13 at the top movement start angle, starts generating X-rays in response to the arrival of the X-ray tube 13 at the exposure start angle, and starts acquiring projection data in response to the arrival of the top 25 at the acquisition start top position. This allows the X-ray computed tomography apparatus 1 to always acquire projection data from the top position or rotational angle in accordance with an instruction from the user regardless of whether helical scanning is performed under different acquisition conditions such as a set top speed and set gantry speed. In addition, when comparing and interpreting a plurality of images associated with a plurality of helical scans under different acquisition conditions, the user can ignore the influence of noise due to the dependence on rotational angles.

According to the above description, the rotational angle detection unit 23 is fixed to the rotating frame 11. However, this embodiment is not limited to this. That is, the rotational angle detection unit 23 may be provided so as to be pivotal about the circumference of the rotating frame 11. In this case, the rotational angle detection unit 23 is slidably provided on a guide rail having almost the same shape as that of the rotating frame 11. The guide rail is accommodated in the gantry 3 at a position near the rotating frame 11. In order to move to an arbitrary rotational angle of the rotating frame 11, the rotational angle detection unit 23 slides on the guide rail upon receiving a driving signal from a motor. For example, the rotational angle detection unit 23 is placed at an angular position on the guide rail which corresponds to the exposure start position or the acquisition start angle. Pivotally providing the rotational angle detection unit 23 in this manner allows to easily move the rotational angle detection unit 23 to an arbitrary angle as compared with the case in which the rotational angle detection unit 23 is fixed.

According to the above description, the apparatus determines an X-ray tube preliminary rotation amount from a top preliminary movement time, and then determines a top movement start angle from the X-ray tube preliminary rotation amount. However, this embodiment is not limited to this. For example, a top movement start angle may be directly determined based on a top preliminary movement time and a set gantry speed.

In the above description, a rotational angle at the estimated time of the stop of generation of X-rays (to be referred to as an exposure stop angle hereinafter) may be set. In this case, in response to the arrival of the X-ray tube 13 at the exposure stop angle, the scan control unit 47 stops generating X-rays under the control of the high voltage generation unit 19. This makes it possible to scan an arbitrary view range.

In the first embodiment, in order to protect an organ susceptible to X-rays, an angle range in which X-ray generation is turned on (to be referred to as an ON range hereinafter) and an angle range in which X-ray generation is turned off (to be referred to as an OFF range hereinafter) may be set. An ON range is defined as the angle range from an acquisition start angle to an acquisition stop angle. An OFF range is defined as the angle range from an acquisition stop angle to an acquisition start angle. For example, an angle range corresponding to almost 240° of 360° may be set as an ON range, and an angle range corresponding to the remaining almost 120° may be set as an OFF range. This setting allows to regularly and repeatedly turn X-ray generation on and off during repetitive rotation of the X-ray tube 13. In this manner, an angle range in which the X-ray tube 13 is located relatively close to an organ susceptible to radiation is set as an OFF range, and an angle range in which the X-ray tube 13 is not located relatively close to the organ is set as an ON range. This makes it possible to execute scanning for a relatively long time while protecting the organ susceptible to radiation.

In addition, in the ON range, the high voltage generation unit 19 may alternately apply a high voltage and a low voltage to the X-ray tube 13 to alternately emit a high dose of X-rays and a low dose of X-rays.

Second Embodiment

An X-ray computed tomography apparatus according to the second embodiment will be described next. The X-ray computed tomography apparatus according to the second embodiment executes conventional scanning. Note that the same reference numerals in the following description denote constituent elements having almost the same functions and arrangements as those in the second embodiment, and a repetitive description will be made only when required.

FIG. 5 is a block diagram showing the arrangement of an X-ray computed tomography apparatus 2 according to the second embodiment. As shown in FIG. 5, the X-ray computed tomography apparatus 2 does not include the top position detection unit 28, the acquisition start top position determination unit 43, and the movement start angle determination unit 45 which are mounted in the X-ray computed tomography apparatus 1 according to the first embodiment.

A scan control unit 57 controls a rotation driving unit 17, a high voltage generation unit 19, and a data acquisition circuit 21 to execute conventional scanning from an acquisition start angle. More specifically, first of all, the scan control unit 57 controls the rotation driving unit 17 to rotate a rotating frame 11 in response to the reception of a rotation start instruction issued by the user via an operation unit 51. The scan control unit 57 controls the high voltage generation unit 19 to generate X-rays in response to the arrival of an X-ray tube 13 at an exposure start angle. The scan control unit 57 then controls the data acquisition circuit 21 to start acquiring projection data in response to the arrival of the X-ray tube 13 at an acquisition start angle.

An example of the operation of the X-ray computed tomography apparatus 2 according to the second embodiment will be described next.

An example of the operation of the X-ray computed tomography apparatus 2 at the stage before conventional scanning will be described first with reference to FIG. 6. The stage before conventional scanning is provided to determine an exposure start angle and an acquisition start angle. Assume that at the stage before conventional scanning, the scan control unit 57 has already set acquisition conditions (scan conditions) such as a set gantry speed and X-ray conditions.

Figure 6:
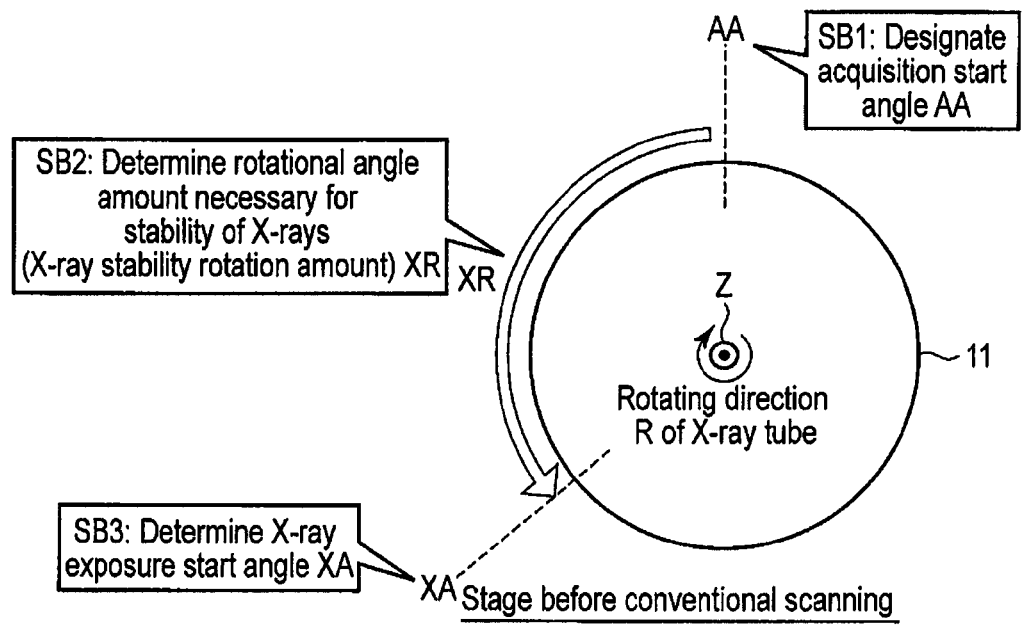
FIG. 6 is a view for explaining an example of operation at the stage before conventional scanning by the X-ray computed tomography apparatus in FIG. 5.

As shown in FIG. 6, at the stage before conventional scanning, first of all, the user designates a rotational angle via the operation unit 51. When the user designates an arbitrary rotational angle, an acquisition start angle determination unit 39 determines the designated rotational angle as an acquisition start angle AA (step SB1).

When the acquisition start angle AA is determined, an exposure start angle determination unit 41 determines an X-ray stability rotation amount based on the acquisition start angle AA and an X-ray stability time (step SB2).

Upon calculating an X-ray stability rotation amount XR, the exposure start angle determination unit 41 determines an X-ray exposure start angle XA based on the acquisition start angle and the rotational angle amount within the X-ray stability time (step SB3).

When an exposure start angle is determined, the stage before conventional scanning is complete.

Figure 7:
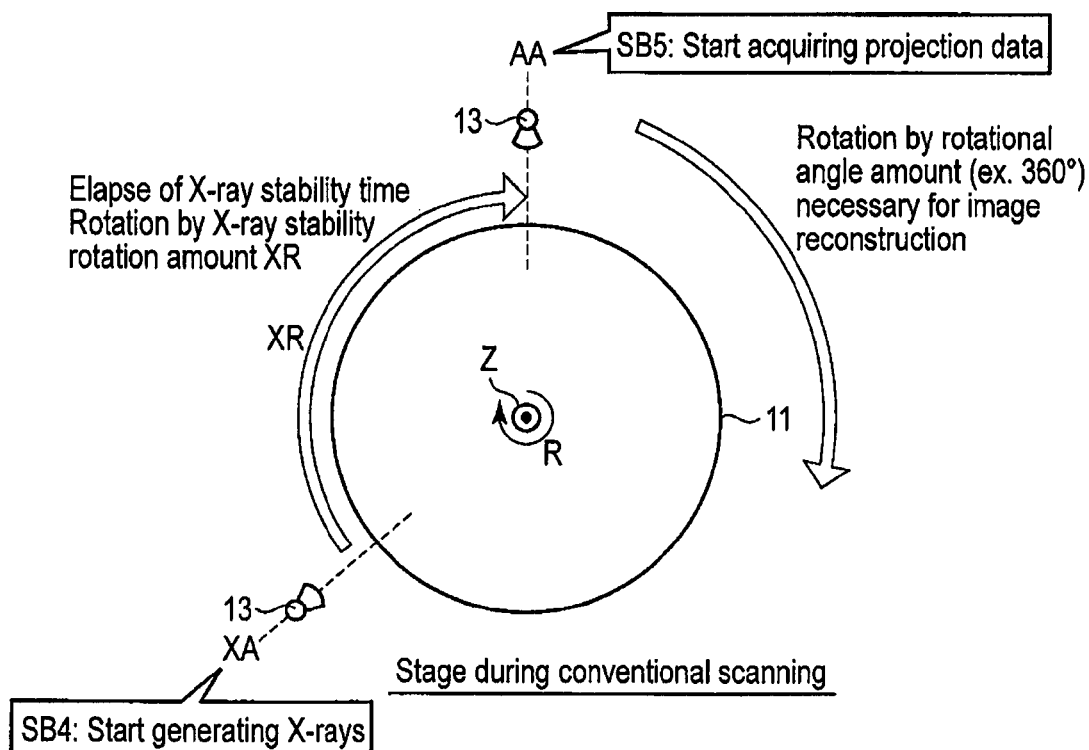
FIG. 7 is a view for explaining an example of operation at the time of execution of conventional scanning by the X-ray computed tomography apparatus in FIG. 5.

An example of the operation of the X-ray computed tomography apparatus 2 at the time of conventional scanning will be described next with reference to FIG. 7. First of all, the user inputs a rotation start instruction for the rotating frame 11 via the operation unit 51 or the like. In response to the reception of the rotation start instruction, the scan control unit 57 controls the rotation driving unit 17 to rotate the rotating frame 11. The rotating frame 11 accelerates until it reaches a set gantry speed from the start of rotation. Thereafter, the rotating frame 11 repeatedly and constantly rotates at the set gantry speed. When the rotational speed reaches the set gantry speed, the X-ray exposure start button of the operation unit 51 shifts to the pressable state. When the user presses the X-ray exposure start button, the scan control unit 57 waits until the X-ray tube 13 reaches the X-ray exposure start angle XA.

In response to the arrival of the X-ray tube 13 at the X-ray exposure start angle XA, the scan control unit 57 controls the high voltage generation unit 19 to generate X-rays from the X-ray tube 13 (step SB4).

When the X-ray tube 13 starts generating X-rays, the scan control unit 57 waits until the arrival of the X-ray tube 13 at the acquisition start angle. When the X-ray tube 13 reaches the acquisition start angle, the scan control unit 57 causes the data acquisition circuit 21 to start acquiring projection data (step SB5). There are two methods of recognizing that the X-ray tube 13 reaches the acquisition start angle AA, that is, methods respectively based on 1. the elapsed time from the exposure start time and 2. the rotational angle of the X-ray tube 13. The two recognition methods will be concretely described below.

Recognition method 2-1: When the X-ray tube 13 reaches the X-ray exposure start angle XA, the scan control unit 57 measures the elapsed time from the exposure start time point (the time point when the X-ray tube 13 has reached the X-ray exposure start angle XA), and waits for the elapse of the X-ray stability time from the exposure start time. In response to the elapse of the X-ray stability time from the exposure start time, the scan control unit 57 causes the data acquisition circuit 21 to start acquiring projection data. The acquisition conditions such as a set top speed and X-ray conditions are not changed at the time of execution of conventional scanning and at the stage before it. Therefore, when the X-ray stability time has elapsed from the exposure start time, the X-ray tube 13 can be regarded to be located at the acquisition start angle AA. That is, the scan control unit 57 regards the elapse of the X-ray stability time from the exposure start time as synonymous with the arrival of the X-ray tube 13 at the acquisition start angle AA. Recognizing the arrival of the X-ray tube 13 at the acquisition start angle AA from the elapsed time from the exposure start time in this manner eliminates the necessity to provide the rotational angle detection unit 23 for detecting an acquisition start angle as in a recognition method 2-2 (to be described later). Therefore, the recognition method 2-1 allows to recognize the arrival of the X-ray tube 13 at the acquisition start angle with a simple arrangement as compared with the recognition method 2-2.

Recognition Method 2-2: In this case, in addition to the rotational angle detection unit 23 for detecting an exposure start angle, the rotational angle detection unit 23 for detecting an acquisition start angle is provided on rotating frame 11. Every time the X-ray tube 13 reaches the acquisition start angle AA, the rotational angle detection unit 23 for detecting an acquisition start angle supplies a rotational angle signal indicating the corresponding information (to be referred to as an acquisition start signal hereinafter) to the scan control unit 57. When the X-ray tube 13 reaches the X-ray exposure start angle XA, the scan control unit 57 waits until an acquisition start angle signal is supplied from the rotational angle detection unit 23 for detecting an acquisition start angle. In response to the reception of an acquisition start signal, the scan control unit 57 causes the data acquisition circuit 21 to start acquiring projection data via the X-ray detector 15. That is, the scan control unit 57 regards the arrival of an acquisition start signal as synonymous with the arrival of the X-ray tube 13 at the acquisition start angle AA. Directly recognizing the arrival of the X-ray tube 13 at the acquisition start angle AA based on the rotational angle of the X-ray tube 13 in this manner allows to start acquiring projection data from the acquisition start angle more reliably than the recognition method 2-1.

When projection data acquisition starts, the scan control unit 57 rotates the X-ray tube 13 by a rotational angle amount necessary for image reconstruction. When the X-ray tube 13 rotates by this rotational angle amount, the scan control unit 57 finishes conventional scanning. That is, the scan control unit 57 controls the high voltage generation unit 19 to make the X-ray tube 13 stop generating X-rays, controls the data acquisition circuit 21 to stop projection data acquisition, and controls the rotation driving unit 17 to stop the rotation of the rotating frame 11.

Note that the image reconstruction methods used by the X-ray computed tomography apparatus 2 include the full-scan method and the half-scan method. In the full-scan method, in order to reconstruct one-slice or volume image data, projection data corresponding to one rotation around the subject P, i.e., about 360°, is required. In the half-scan method, in order to reconstruct one-volume image data, projection data corresponding to $180°\pm\alpha$ ($\alpha$: fan angle) is required. This embodiment can use either of the full-scan method and the half-scan method.

The X-ray computed tomography apparatus 2 according to the second embodiment determines an arbitrary rotational angle as an acquisition start angle in accordance with an instruction from the user in conventional scanning. The X-ray computed tomography apparatus 1 determines an exposure start angle based on the determined acquisition start angle and the X-ray stability time. The X-ray computed tomography apparatus 2 causes the X-ray tube 13 to generate X-rays in response to the arrival of the X-ray tube 13 at the exposure start angle, and causes the data acquisition circuit 21 to start acquiring projection data in response to the arrival of the X-ray tube 13 at the acquisition start angle. This allows the X-ray computed tomography apparatus 2 to always acquire projection data from the rotational angle in accordance with an instruction from the user regardless of whether conventional scanning is performed under different acquisition conditions such as a set top speed and X-ray conditions. It is therefore possible to acquire projection data while avoiding applying X-rays to the surface of an organ susceptible to radiation. Noise corresponding to a rotational angle sometimes occurs in a reconstructed image. However, according to the second embodiment, since it is possible to always acquire projection data from the same rotational angle regardless of acquisition conditions, when comparing and interpreting a plurality of images associated with a plurality of conventional scans under different acquisition conditions, the user can ignore the influence of noise due to the dependence on rotational angles.

The X-ray computed tomography apparatus according to this embodiment, therefore, can start acquiring projection data from an arbitrary top position or rotational angle.

Modification

As described above, the X-ray computed tomography apparatuses according to the first and second embodiments each include the gantry 3 and the console 5. However, the X-ray computed tomography apparatus according to this embodiment is not limited to this. For example, as shown in FIG. 8, the X-ray computed tomography apparatus 1 may include a gantry controller 7 in addition to the gantry 3 and the console 5. As in the first embodiment, in the case of the X-ray computed tomography apparatus 1 having the helical scan function, the gantry controller 7 includes the input unit 31, the acquisition start angle determination unit 39, the exposure start angle determination unit 41, the acquisition start top position determination unit 43, the movement start angle determination unit 45, and the scan control unit 47. This arrangement allows the gantry controller 7 to take charge of the scan control function according to this embodiment while the function is omitted from the console 5. This makes it possible to implement the scan control function according to this embodiment in the X-ray computed tomography apparatus at a low cost. In the case of the X-ray computed tomography apparatus 1 without any helical scan function as in the second embodiment, the gantry controller 7 may include the input unit 31, the acquisition start angle determination unit 39, the exposure start angle determination unit 41, and the scan control unit 47.

Some embodiments of the present invention have been described above. However, these embodiments are presented merely as examples and are not intended to restrict the scope of the invention. These novel embodiments can be carried out in various other forms, and various omissions, replacements, and alterations can be made without departing from the gist of the invention. The embodiments and their modifications are also included in the spirit and scope of the invention as well as in the invention described in the claims and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
an X-ray tube configured to generate X-rays;
a detector configured to detect X-rays which are generated from the X-ray tube and transmitted through a subject;
a first support mechanism configured to rotatably support the X-ray tube and the detector;
a first driving unit configured to drive the first support mechanism to rotate the X-ray tube and the detector around the subject;
a top on which the subject is placed;
a second support mechanism configured to movably support the top;
a second driving unit configured to drive the second support mechanism to move the top;
an acquisition unit configured to acquire projection data associated with the subject via the detector;
a position determination unit configured to determine a position of the top at an estimated start time of projection data acquisition by the acquisition unit;
a first angle determination unit configured to determine a first rotational angle of the X-ray tube at the estimated start time of projection data acquisition;
a second angle determination unit configured to determine a second rotational angle of the X-ray tube at an estimated start time of movement of the top based on the determined first rotational angle and a time interval from the estimated start time of movement to the estimated start time of projection data acquisition; and
a control unit configured to control the first driving unit to rotate the X-ray tube around the subject, control the second driving unit to make the top start moving in response to arrival of the X-ray tube at the determined second rotational angle, and control the acquisition unit to start acquiring projection data in response to arrival of the top at the determined position of the top.

2. The X-ray computed tomography apparatus of claim 1, wherein the control unit causes the acquisition unit to start acquiring projection data in response to an elapse of an X-ray stability time from a time point when the X-ray tube reaches the second rotational angle.

3. The X-ray computed tomography apparatus of claim 1, wherein the second angle determination unit calculates the time interval based on the position of the top.

4. The X-ray computed tomography apparatus of claim 1, wherein the second angle determination unit determines a rotation amount of the X-ray tube over the time interval based on the time interval and a preset X-ray tube rotational speed, and determines the second rotational angle based on the rotation amount and the first rotational angle.

5. The X-ray computed tomography apparatus of claim 1, wherein the position determination unit is further configured to determine the position of the top in accordance with an instruction from a user.

6. The X-ray computed tomography apparatus of claim 1, wherein the first angle determination unit is further configured to determine the first rotational angle of the X-ray tube in accordance with an instruction from a user.

* * * * *